(12) United States Patent
Takehana et al.

(10) Patent No.: US 6,303,655 B1
(45) Date of Patent: Oct. 16, 2001

(54) PREVENTIVES OR REMEDIES FOR DISEASES AFFECTING EXCESSIVE PROLIFERATION OF RETINAL PIGMENT EPITHELIAL CELLS

(75) Inventors: Yasuo Takehana; Makio Kitazawa, both of Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 09/403,010
(22) PCT Filed: Apr. 10, 1998
(86) PCT No.: PCT/JP98/01654
§ 371 Date: Oct. 18, 1999
§ 102(e) Date: Oct. 18, 1999
(87) PCT Pub. No.: WO98/47504
PCT Pub. Date: Oct. 29, 1998

(30) Foreign Application Priority Data

Apr. 18, 1997 (JP) .................................................. 9-135675

(51) Int. Cl.⁷ .................................................. A61K 31/195
(52) U.S. Cl. .................................................. 514/563; 514/912
(58) Field of Search ...................................... 514/563, 912

(56) References Cited

PUBLICATIONS

Chemical Abstracts 126:288094. Okamoto, 1997.*

* cited by examiner

Primary Examiner—Zohreh Fay
(74) Attorney, Agent, or Firm—Stuart D. Frenkel; Liniak, Berenato, Longacre & White

(57) ABSTRACT

The present invention relates to an agent for the prevention or treatment of diseases associated with excessive proliferation of retinal pigment epithelial cells such as proliferative vitreoretinopathy comprising as the active ingredient N-(3,4-dimethoxycinnamoyl)anthranilic acid represented by the formula:

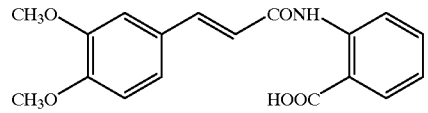

or a pharmaceutically acceptable salt thereof, which has an inhibitory activity on proliferation of retinal pigment epithelial cells.

8 Claims, No Drawings

PREVENTIVES OR REMEDIES FOR DISEASES AFFECTING EXCESSIVE PROLIFERATION OF RETINAL PIGMENT EPITHELIAL CELLS

FIELD OF THE INVENTION

The present invention relates to a pharmaceutical composition which is useful as an agent for the prevention or treatment of diseases associated with excessive proliferation of retinal pigment epithelial cells.

More particularly, the present invention relates to an agent for the prevention or treatment of diseases associated with excessive proliferation of retinal pigment epithelial cells, which comprises as the active ingredient N-(3,4-dimethoxy-cinnamoyl)anthranilic acid (generic name: Tranilast) represented by the formula:

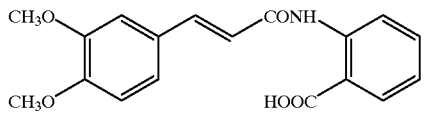

or a pharmaceutically acceptable salt thereof.

In the present invention, as diseases associated with excessive proliferation of retinal pigment epithelial cells, proliferative vitreoretinopathy can be exemplified.

BACKGROUND OF THE INVENTION

In surgical retinopexy performed as a remedy for retinal detachment, proliferative vitreoretinopathy, a disease associated with excessive proliferation of retinal pigment epithelial cells, is known to remain as a cause of worsening prognosis. At the present time, only vitreous surgery has been used as a remedy for such proliferative vitreoretinopathy. Under present conditions, visual prognosis is not necessarily said to be favorable even after the surgery. It is well known that the proliferation of retinal pigment epithelial cells plays an important role in the occurrence and development of such proliferative vitreoretinopathy. Many researchers have studied the inhibitory effects of various drugs on proliferation of retinal pigment epithelial cells (Japanese Review of Clinical Ophthalmology, Vol. 9, pp. 1886–1890 (1993); Japanese Review of Clinical Ophthalmology, Vol. 9, pp. 2030–2034 (1993).

On the other hand, the technical progress of vitreous surgery has resulted in remarkable improvements in the cure rate of retinal detachment. However, a limit of the cure rate is said to be 92–94%. It is thought that proliferative vitreoretinopathy, namely, proliferation of retinal pigment epithelial cells largely participates as the cause of limiting the cure rate. Therefore, development of drugs having excellent inhibitory effects on excessive proliferation or retinal pigment epithelial cells have been desired to improve the cure rate of retinopexy for retinal detachment and for the prevention or treatment of proliferative vitreoretinopathy.

Tranilast has been used widely as a drug for the treatment of allergic disorders such as bronchial asthma, allergic rhinitis, atopic dermatitis and allergic conjunctivitis, and cutaneous disorders such as keloid and hypertrophic scar. For example, it has been known that Tranilast has inhibitory effects on chemical mediator release caused by an allergic reaction, excessive collagen accumulation by fibroblast cells in cutaneous tissues and excessive proliferation of smooth muscle cells in coronary artery vessels.

However, it has not been disclosed that Tranilast suppresses proliferation of retinal pigment epithelial cells and is therefore useful as an agent for the prevention or treatment of proliferative vitreoretinopathy.

SUMMARY OF THE INVENTION

The present invention relates to an agent for the prevention or treatment of diseases associated with excessive proliferation of retinal pigment epithelial cells, which comprises as the active ingredient N-(3,4-dimethoxy-cinnamoyl) anthranilic acid represented by the formula:

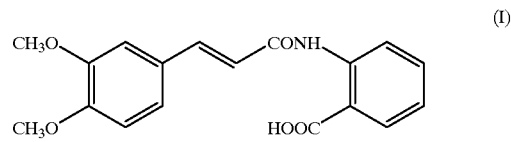

or a pharmaceutically acceptable salt thereof.

The present invention relates to a method for the prevention or treatment of diseases associated with excessive proliferation of retinal pigment epithelial cells, which comprises administering N-(3,4-dimethoxycinnamoyl) anthranilic acid represented by the above formula (I) or a pharmaceutically acceptable salt thereof.

The present invention relates to a use of N-(3,4-dimethoxycinnamoyl)anthranilic acid represented by the above formula (I) or a pharmaceutically acceptable salt thereof for the manufacture of a pharmaceutical composition for the prevention and treatment of diseases associated with excessive proliferation of retinal pigment epithelial cells.

Furthermore, the present invention relates to a use of N-(3,4-dimethoxycinnamoyl)anthranilic acid represented by the above formula (I) or a pharmaceutically acceptable salt thereof as an agent for the prevention or treatment of diseases associated with excessive proliferation of retinal pigment epithelial cells.

The present inventors have studied earnestly to find compounds having inhibitory effects on excessive proliferation of retinal pigment epithelial cells. As a result, it was found that Tranilast has a marked inhibitory effect on proliferation of retinal pigment epithelial cells, and therefore, is extremely useful as an agent for the prevention or treatment of diseases associated with excessive proliferation of retinal pigment epithelial cells, thereby forming the basis of the present invention.

Accordingly, the present inventors confirmed that Tranilast markedly suppressed proliferation of retinal pigment epithelial cells in the in vitro cell proliferation inhibitory effect test using rat retinal pigment epithelial cells.

DETAILED DESCRIPTION OF THE INVENTION

Tranilast has been found to provide an excellent inhibitory effect on proliferation of retinal pigment epithelial cells, and therefore, is a compound useful as an agent for the prevention or treatment of diseases associated with excessive proliferation of retinal pigment epithelial cells.

Therefore, pharmaceutical compositions which are useful as agents for the prevention or treatment of diseases associated with excessive proliferation of retinal pigment epithelial cells can be prepared by comprising as the active ingredient Tranilast or a pharmaceutically acceptable salt thereof.

Various methods for the preparation of Tranilast and pharmaceutically acceptable salts thereof which are active ingredients are known, and they can be readily prepared by methods described in patent literature and the like (Japanese Patent Application Publication (kokoku) No. Sho. 56-40710; ibid. No. Sho. 57-36905; ibid. No. Sho. 58-17186; ibid. No. Sho. 58-48545; ibid. No. Sho. 58-55138; ibid. No. Sho. 58-55139; ibid. No. Hei. 1-28013; ibid. No. Hei. 1-50219; ibid. No. Hei. 3-37539 etc.).

As examples of pharmaceutically acceptable salts of Tranilast, salts with inorganic bases such as a sodium salt and a potassium salt, salts formed with organic amines such as morpholine, piperidine, piperazine and pyrrolidine and salts formed with amino acids can be illustrated.

When the pharmaceutical compositions of the present invention are employed in a practical treatment, the composition may be administered orally. A topical administration such as eye drops, eye ointments or injections is preferable.

For example, eye drops can be formulated by dissolving Tranilast or a pharmaceutically acceptable salt thereof together with a basic substance with heating in a proper quantity of sterilized water in which a surface active agent is dissolved, adding polyvinylpyrrolidone, and optionally adding appropriate pharmaceutical additives such as a preservative, a stabilizing agent, a buffer, an isotonicity, an antioxidant and a viscosity improver, and dissolving the additives completely.

For example, eye ointments can be appropriately formulated by using bases which are generally used in eye ointments. Eye ointments can be also used as reversible thermally gelling water-base pharmaceutical compositions.

For example, injections can be injected directly into diseased tissues such as vitreous or adjacent tissues by using a fine needle, and can be also used as intraocular perfusate.

The pharmaceutical compositions of the present invention can be administered as sustained release preparations. For example, a Tranilast preparation can be incorporated into a pellet or microcapsule of sustained release polymer as a sustained release preparation, and the pellet or microcapsule surgically implanted into the tissues to be treated. As examples of sustained release polymers, ethylene-vinylacatate copolymer, polyhydro-methacrylate, polyacrylamide, polyvinylpyrrolidone, methyl-cellulose, lactic acid polymer, lactic acid-glycolic acid copolymer and the like can be illustrated. Preferably, a biodegradable polymer such as lactic acid polymer and lactic acid-glycolic acid copolymer can be illustrated.

When the pharmaceutical compositions of the present invention are employed in a practical treatment, the dosage of Tranilast or a pharmaceutically acceptable salt thereof as the active ingredient is appropriately decided depending on the age, degree of symptoms of each patent to be treated, therapeutic value and the like. The dosage should be fixed at an appropriate concentration to be curable. For example, in case of eye drops, preferably 0.001–2 weight % eye drops are instilled one to several times per day and applied one to several droplets per time.

EXAMPLES

The present invention is further illustrated in more detail by way of the following Examples.

Test to Confirm Inhibitory Effects on Proliferation of Retinal Pigment Epithelial Cells (1) Isolation and Cultivation of Retinal Pigment Epithelial Cells Isolation and cultivation of retinal epithelial cells from rats were performed as described by Sakagami et al. (Ophthalmic Res., Vol. 27, pp. 262–267 (1995)). Six-days old Brown Norway rats were anesthetized with an intraperitoneal injection of pentobarbital and the eyes were removed. After dipping in 70% ethanol for sterilization, the eyes were rinsed in Hanks' balanced salt solution (HBSS). They were incubated for 15 minutes at 37° C. in 0.1% proteinase K solution. After incubation, the eyeballs were rinsed in HBSS and placed in a dish containing 1:1 Dulbecco's modified Eagle's Medium (DMEM):Ham's F12 medium supplemented with 10% fetal bovine serum (FBS). A circumferential incision was made just below the ora serrata of each eye. Then the anterior segment, the lens and the vitreous were removed and discarded. Under a stereoscopic microscope, the retinal pigment epithelial cells were lifted from the retina. Sheets of retinal pigment epithelial cells were washed in calcium- and magnesium-free HBSS. After the sheets of retinal pigment epithelial cells had been incubated in 0.1% trypsin solution for 7 minutes at 37° C., a Pasteur pipette was used to isolate the cells. The isolated cells were cultured in 1:1 DMEM:Ham's F12 medium supplemented with 10% fetal bovine serum (FBS) and used in further experiments.

(2) Preparation of Test Drugs

Test drugs were prepared by dissolving Tranilast in dimethyl sulfoxide (DMSO) and diluting the solution with a medium for endothelial cell culture to a final prescribed concentration. The final concentration of DMSO was 0.5%.

(3) Experimental Method

A cell suspension (200 $\mu$l) containing $4 \times 10^4$ cells was added to each well of a collagen-coated 96-well plate and cultured at 37° C. under an atmosphere of 5% $CO_2$ in air. After 1 day, the medium was replaced and cultured with 200 $\mu$l of 1:1 DMEM:Ham's F12 medium supplemented with 10% FBS containing various concentrations of Tranilast. After 4 days, 20 $\mu$l of Alamar-Blue, a reagent for assaying cell proliferation, was added to each well. After 4 hours incubation, the absorbance at 620 nm was measured by immnoreader and the number of cells was calculated.

(4) Assessment of Effect

The number of cells in the non-treated group was expressed as 100%, and inhibitory rates of cell proliferation in the groups treated with various concentrations of Tranilast were calculated.

(5) Results

As shown in the following Table, Tranilast markedly suppressed the proliferation of retinal pigment epithelial cells in a concentration-dependent manner.

| Added amount of Tranilast ($\mu$g/ml) | Inhibitory rate of retinal pigment epithelial cell proliferation (%) |
| --- | --- |
| 25 | 7.1 |
| 50 | 30.2 |
| 100 | 84.6 |

A pharmaceutical composition comprising as the active ingredient Tranilast or a pharmaceutically acceptable salt thereof has a marked inhibitory activity on proliferation of retinal pigment epithelial cells, and therefore, is extremely suitable as an agent for the prevention or treatment of diseases associated with excessive proliferation of retinal pigment epithelial cells such as proliferative vitreoretinopathy.

What is claimed is:

1. A method for the treatment of diseases associated with excessive proliferation of retinal pigment epithelial cells "or prevention of said diseases dubsequent to surgical retinopexy" which comprises administering N-(3,4-dimethoxycinnamoyl)anthranilic acid represented by the formula:

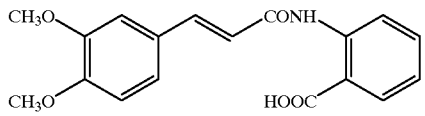

or a pharmaceutically acceptable salt thereof.

2. The method of claim 1, wherein said diseases associated with excessive proliferation of retinal pigment epithelial cells include proliferative vitreoretinopathy.

3. The method of claim 1, wherein said N-(3,4-dimethoxycinnamoyl) anthranilic acid is administered in the form of eye drops.

4. The method of claim 1, wherein said N-(3,4-dimethoxycinnamoyl) anthranilic acid is administered in the form of eye ointments.

5. The method of claim 1, wherein said N-(3,4-dimethoxycinnamoyl) anthranilic acid is administered in the form of a surgical implant.

6. The method of claim 5, wherein said surgical implant comprises a sustained release preparation.

7. The method of claim 1, wherein said N-(3,4-dimethoxycinnamoyl) anthranilic acid is administered orally.

8. The method of claim 1, wherein said N-(3,4-dimethoxycinnamoyl) anthranilic acid is administered in the form of an injection into diseased tissues.

* * * * *

UNITED STATES PATENT AND TRADEMARK OFFICE
CERTIFICATE OF CORRECTION

PATENT NO. : 6,303,655 B1
DATED : October 16, 2001
INVENTOR(S) : Yasuo Takehana and Makio Kitazawa It is certified that error appears in the above-identified patent and that said Letters Patent is hereby corrected as shown below:

Column 4,
Line 67, delete the quotation mark.

Column 5,
Line 1, change "dubsequent" to -- subsequent --.
Line 2, delete the quotation mark.

Signed and Sealed this

Ninth Day of April, 2002

Attest:

JAMES E. ROGAN
Attesting Officer   Director of the United States Patent and Trademark Office